United States Patent [19]
Frischkorn et al.

[11] 4,376,214
[45] Mar. 8, 1983

[54] PROCESS FOR THE PREPARATION OF NAPHTHALENE-1,4-DICARBOXYLIC ACID

[75] Inventors: Hans Frischkorn; Erich Schinzel, both of Hofheim am Taunus, Fed. Rep. of Germany

[73] Assignee: Hoechst Aktiengesellschaft, Frankfurt, Fed. Rep. of Germany

[21] Appl. No.: 275,921

[22] Filed: Jun. 22, 1981

[30] Foreign Application Priority Data

Jul. 2, 1980 [DE] Fed. Rep. of Germany ....... 3025016

[51] Int. Cl.³ ............................................. C07C 51/08
[52] U.S. Cl. ................................. 562/484; 260/438.1; 260/465 D

[58] Field of Search ..................... 562/484; 260/438.1, 260/465 D

[56] References Cited

U.S. PATENT DOCUMENTS 3,393,220 7/1968 Winnick et al. ..................... 562/484

Primary Examiner—Natalie Trousof
Assistant Examiner—Vera C. Clarke
Attorney, Agent, or Firm—Connolly and Hutz

[57] ABSTRACT

Process for the preparation of naphthalene-1,4-dicarboxylic acid, wherein 4-bromo-1-naphthoic acid is reacted with at least 1 mole of copper-(I) cyanide per mole of 4-bromonaphthoic acid in a polar, aprotic solvent, and the copper salt complex of 4-cyanonaphthoic acid thus obtained is saponified in an alkaline medium.

3 Claims, No Drawings

PROCESS FOR THE PREPARATION OF NAPHTHALENE-1,4-DICARBOXYLIC ACID

The preparation of naphthalene-1,4-dicarboxylic acid by saponification of 1,4-dicyanonaphthalene is already known [see R. Scholl and H. Neumann, Ber. 55 (1922), 121 and E. F. Bradbrook and R. P. Linstead, J. chem. soc. (London) 1936, 1739-1744]. The processes described in these references for the preparation of the dinitrile start from suitable naphthalenesulfonic acids, which are converted to 1,4-dicyanonaphthalene by fusion with potassium cyanide. These processes, however, require extreme conditions, produce to a relatively large extent dark colored by-products and are, therefore, little suited to an industrial production of naphthalene-1,4-dicarboxylic acid.

It has now been found that naphthalene-1,4-dicarboxylic acid may be prepared in high purity and in a manner well suited to industrial application, if 4-bromo-1-naphthoic acid is reacted with at least 1 mole of copper-(I) cyanide per mole of 4-bromonaphthoic acid in polar aprotic solvents, if appropriate in the presence of catalytic amounts of potassium iodide and copper sulfate, and the copper salt complex of the 4-cyanonaphthoic acid thus obtained is saponified in an alkaline medium.

The 4-bromo-1-naphthoic acid required as starting material according to the process according to the invention has already been described in the literature. It can, for example, be prepared in a simple manner by reacting 1-bromonaphthalene with acetyl chloride in a Friedel-Crafts reaction to give 4-bromo-1-acetylnaphthalene (see K. Dziewouski and L. Sternback, Bull. acad. polonaise A, 1931, 59 to 68, or T. L. Jacobs, S. Winstein, J. W. Ralls and J. H. Robson Journ. org. chem. 11 (1946), 27-33) and by oxidation of the latter compound with hypochlorite [see T. L. Jacobs et. al, see above, or N. J. Leonard and A. M. Hyson, J. Am. chem. soc. 71 (1949), 1963].

The amount of copper-(I) cyanide employed varies between 1 and 1.5 mole, relative to 1 mole of 4-bromonaphthoic acid. N-methylacetamide, dimethylacetamide, dimethylsulfoxide, N-methylpyrrolidone, hexamethylphosphoric acid triamide, quinaldine and preferably dimethylformamide and quinoline are used as the polar aprotic solvent.

The reaction is carried out at temperatures of 150°-250° C., advantageously at the boiling point of the solvent employed. In addition, it is advantageous to accelerate the reaction by addition of a catalyst. A mixture of potassium iodide and copper sulfate may be taken for this purpose.

In this reaction, the 4-cyanonaphthoic acid is formed as the copper-(I) salt complex of the following composition

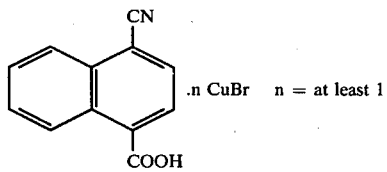

.n CuBr    n = at least 1 which can be isolated after cooling down the reaction mixture and after addition of water or a low boiling solvent. Lower alcohols, preferably methanol or ethanol, are employed as the low boiling polar solvent.

Without liberating the 4-cyanonaphthoic acid, the still moist copper salt complex is then directly saponified in an alkaline medium, according to known methods, using a strong alkali, for example with excess 10-35% strength sodium hydroxide solution at boiling heat. The pH value of the solution is then adjusted to 7 to 8 and the copper oxide quantitatively precipitated thereby is separated off. By further addition of mineral acid, to pH 2, the naphthalene dicarboxylic acid is precipitated from the filtrate, and is separated off.

The working-up process can also be carried out in such a manner that the isolation of the copper salt complex of 4-cyanonaphthoic acid is omitted and, after termination of the halogen/cyanide exchange, the reaction mixture is directly hydrolyzed with strong alkali, such as approximately 10-35% strength sodium hydroxide solution.

If quinoline or quinaldine is used as the solvent in the process, it can be distilled off by means of steam during the hydrolysis.

The naphthalene-1,4-dicarboxylic acid obtained according to the process according to the invention is used as an intermediate for dyestuffs, UV absorbers, scintillators and optical brighteners. It is free from colored impurities and can be directly employed for further synthesis.

The following examples illustrate the invention in more detail. Temperatures are given in °C.

EXAMPLE 1

125.6 parts by weight of 4-bromo-1-naphthoic acid with a melting point of 219°-220° and 51 parts by weight of copper-(I) cyanide (67-71% copper) are introduced into 330 parts by weight of dimethylformamide. The mixture is then heated under reflux for 4 hours, whilst stirring, to 150°-160° C., whereby, after some time, the solid materials go into solution, but then the 4-cyano-1-naphthoic acid copper bromide complex is gradually precipitated. After cooling to about 100°, the reaction mixture is diluted with 330 parts by weight of water and stirred for approximately one hour at room temperature, and the precipitate is filtered off by suction and rinsed with about 400 parts by weight of water. The 4-cyanonaphthoic acid/copper bromide complex thus isolated is introduced into 550 parts by weight of 20% sodium hydroxide solution and heated under reflux for 5 hours. The mixture is then adjusted to pH 7.0-7.5 with about 220 parts by weight of concentrated hydrochloric acid, the solution is filtered off by suction from the copper oxide slurry deposited and this slurry is rinsed with about 500 parts by weight of water, in portions. The naphthalene-1,4-dicarboxylic acid is precipitated from the filtrate at pH 2 by the addition of about 100 parts by weight of concentrated hydrochloric acid, and the precipitate is filtered off under suction and is washed with water until free of chloride ions. After drying, 92 parts by weight of a practically colorless naphthalene-1,4-dicarboxylic acid with a melting point of 315°-320° are obtained.

The 4-bromo-1-naphthoic acid employed can be prepared as follows:

160 parts by weight of aluminum chloride and subsequently 94 parts by weight of acetyl chloride are introduced into 500 parts by volume of dry ethylene chloride. The mixture is stirred at 30°-35° until a clear solution has formed. Only at this point are 207 parts by weight of 1-bromonaphthalene, dissolved in 250 parts by volume of ethylene chloride, added to the solution at about 40° in the course of 15 minutes, and the mixture is stirred for 30 minutes at about 90°. The mixture is cooled to room temperature, and the precipitated aluminum chloride/4-bromo-1-acetyl-naphthalene complex is filtered off under suction and washed several times with a little ethylene chloride. The resulting complex is introduced into 2,000 parts by volume of 2 normal hydrochloric acid and this is decomposed by heating to 100°, the ethylene chloride introduced with the complex being distilled off at the same time. After cooling to room temperature, whilst stirring, 4-bromo-1-acetyl-naphthalene is deposited in the form of crystals. The crystals are filtered off under suction and the adhering acid is washed out well with water, the residue being ground with water if necessary; after drying, 207 parts by weight of an almost colorless product of melting point 46°–48° are obtained.

The 4-bromo-1-acetylnaphthalene thus obtained is introduced, if necessary still moist, into 2,000 parts by weight of water and the reaction mixture is heated to 90°, whilst about 70 parts by weight of concentrated sodium hydroxide solution and 0.1 part by weight of a dispersion agent are added. 2,000 parts by volume of chlorine bleach liquor (containing 14% of active chlorine) are then allowed to flow into the reaction mixture in the course of from 2 to 3 hours, and the chloroform formed is distilled off over a descending condenser. After a further reaction time of one hour, about 100 parts by volume of a 40% strength sodium bisulfite solution are added, the solution formed is clarified after addition of 5 parts by weight of active charcoal and is acidified to pH 2 with about 80 parts by weight of concentrated hydrochloric acid. The precipitated 4-bromo-1-naphthoic acid is filtered off under suction, washed with water until free of chloride ions and dried. 187 parts by weight of an almost colorless acid of melting point 219°–220° are obtained.

EXAMPLE 2

125.6 parts by weight of 4-bromo-1-naphthoic acid of melting point 219°–220° and 51 parts by weight of copper-(I) cyanide (67–71% copper) are introduced into 330 parts by weight of anhydrous quinoline. The mixture is then heated under reflux to 235°–240° for 4 hours, whilst stirring, and a homogeneous dark solution is formed. After cooling to about 120°, 750 parts by weight of a 15% strength sodium hydroxide solution are added to the reaction mixture and the yellowish brown suspension formed is heated under reflux, and the condensation products are conducted over a suitable phase separation apparatus and the phase of higher specific gravity—quinoline containing water—is removed. After complete hydrolysis of the 4-cyano-1-naphthoic acid copper salt complex or complete removal of the quinoline (after about 6 hours), the reaction mixture is allowed to cool to 80°, neutralized to pH 7.0–7.5 with about 230 parts by weight of concentrated hydrochloric acid, and filtered off under suction from the copper oxide slurry deposited, the latter being rinsed with about 500 parts by weight of water. The naphthalene-1,4-dicarboxylic acid is precipitated from the filtrate at pH 2 by addition of about 90 parts by weight of concentrated hydrochloric acid, and the precipitate is filtered off under suction and washed with water until free of chloride ions. After drying, 90 parts by weight of a practically colorless acid with a melting point of 315°–320° are obtained.

We claim:

1. Process for the preparation of naphthalene-1,4-dicarboxylic acid, wherein 4-bromo-1-naphthoic acid is reacted with at least 1 mole of copper-(I) cyanide per mole of 4-bromonaphthoic acid in a polar, aprotic solvent at a temperature of 150°–250° C. and the copper salt complex of 4-cyanonaphthoic acid thus obtained is saponified in an alkaline medium.

2. Process as claimed in claim 1, wherein the copper salt complex of 4-cyanonaphthoic acid is precipitated by addition of water or a low boiling polar solvent, is separated off and is saponified.

3. Process as claimed in claim 1, wherein the copper salt complex of 4-cyanonaphthoic acid is directly hydrolyzed in the reaction mixture, after the cyanide exchange, without previous isolation.

* * * * *